United States Patent
Prince

(10) Patent No.: US 6,738,505 B1
(45) Date of Patent: May 18, 2004

(54) METHOD AND APPARATUS FOR DETECTING SOLDER PASTE DEPOSITS ON SUBSTRATES

(75) Inventor: David P. Prince, Wakefield, RI (US)

(73) Assignee: Speedline Technologies, Inc., Franklin, MA (US)

(*) Notice: Subject to any disclaimer, the term of this patent is extended or adjusted under 35 U.S.C. 154(b) by 0 days.

(21) Appl. No.: 09/304,699

(22) Filed: May 4, 1999

(51) Int. Cl.[7] ............................. G06K 9/00; G01N 21/00
(52) U.S. Cl. ..................... 382/150; 382/151; 356/237.5
(58) Field of Search ................................. 382/173, 256, 382/263, 264, 274, 141, 143–151; 348/86, 87, 125, 126, 127; 118/213; 702/35, 36; 356/237.1, 239.3, 237.5, 237.4

(56) References Cited

U.S. PATENT DOCUMENTS

| | | | |
|---|---|---|---|
| 5,172,420 A | 12/1992 | Ray et al. | 382/150 |
| 5,455,870 A | 10/1995 | Sepai et al. | 382/147 |
| 5,801,965 A * | 9/1998 | Takagi et al. | 702/35 |
| 5,873,939 A * | 2/1999 | Doyle et al. | 118/213 |
| 6,362,877 B1 * | 3/2002 | Kobayashi et al. | 356/237.5 |

FOREIGN PATENT DOCUMENTS

| | | |
|---|---|---|
| GB | 2 286 670 | 8/1995 |
| WO | WO 95/16247 | 6/1995 |
| WO | WO 98/37741 | 8/1998 |

OTHER PUBLICATIONS

Ritter, Gerhard, X., et al., *Handbook of Computer Vision Algorithms in Image Algebra*, CRC Press, Inc., Boca Raton, FL (1996), Ch. 2, 3 and 4 (pp. 51–141).
Russ, John C., *The Image Processing Handbook*, 2$^{nd}$ Edition, CRC Press, Inc., Boca Raton, FL (1995), pp. 155–160, 211–237, 259–262, 361–371, 481–500.
Cognex Press Release, *Cognex Introduces New Machine Vision System for Detecting Screen Printing Defects On Printed Circuit Boards*, (2 pgs); http://www.cognex.com/press/release/products/pasteinspect.htm.

* cited by examiner

*Primary Examiner*—Vikkram Bali
(74) *Attorney, Agent, or Firm*—Mintz, Levin, Cohn, Ferris, Glovsky and Popeo, P.C.

(57) ABSTRACT

The invention relates to a method and apparatus for inspecting a substrate having a substance deposited thereon. The steps of the method include depositing the substance onto the substrate; capturing an image of the substrate; detecting variations in texture in the image to determine a location of the substance on the substrate; and comparing the location of the substance with a desired location. The apparatus includes a screen printer that dispenses a substance at a predetermined location on a substrate, and a machine vision inspection system that includes texture based recognition of the substance.

27 Claims, 14 Drawing Sheets

Fig. 5A

|   | 1 |   |
|---|---|---|
| 1 | -4 | 1 |
|   | 1 |   |

Fig. 5B

|   | -1 |   |
|---|---|---|
| -1 | 5 | -1 |
|   | -1 |   |

Fig. 5C

| 1 | 1 | 1 |
|---|---|---|
| 1 | 1 | 1 |
| 1 | 1 | 1 |

Ø0.9594

Ø1.3568

Ø1.9188

Ø2.7136

METHOD AND APPARATUS FOR DETECTING SOLDER PASTE DEPOSITS ON SUBSTRATES

FIELD OF THE INVENTION

The present invention relates to machine vision processes, and more particularly to a method and apparatus for inspecting solder paste deposited on a substrate using a solder paste printing or dispensing machine. In addition, the present invention relates to methods and apparatuses for controlling solder paste printers and dispensing machines.

BACKGROUND OF THE INVENTION

In typical surface-mount circuit board manufacturing operations, a stencil printer is used to print solder paste onto a circuit board. Typically, a circuit board having a pattern of pads or some other, usually conductive, surface onto which solder paste will be deposited is automatically fed into the stencil printer and one or more small holes or marks on the circuit board, called fiducials, is used to properly align the circuit board with the stencil or screen of the stencil printer prior to the printing of solder paste onto the circuit board. In some prior art systems, an optical alignment system is used to align the circuit board with the stencil. Examples of optical alignment systems for stencil printers are described in U.S. Pat. No. 5,060,063, issued Oct. 21, 1991 to Freeman, and in U.S. Pat. No. Re. 34,615 issued Jan. 31, 1992, also to Freeman, each of which is incorporated herein by reference.

In some prior art systems, the optical alignment system also includes a vision inspection system to inspect a substrate after solder paste has been deposited thereon. These prior art systems generally rely on thresholding techniques to inspect a substrate having solder paste deposited thereon to determine whether the solder paste has been properly applied to conductive pads strategically located on the substrate. As is well known in the art, thresholding is an image segmentation technique used to divide an image into sections based on brightness. The technique segments an image into regions of interest and removes all other regions deemed not essential.

At present, most common techniques for identifying solder paste regions on a printed circuit board primarily consist of single or dual thresholding methods that typically use pixel brightness to identify solder paste regions on a substrate. One drawback of these techniques is that brightness levels of the solder paste and the background often overlap making it difficult, if not impossible, to effectively separate the solder paste images from background information.

Some prior art systems rely primarily on subtraction techniques that require a unique reference image for each inspection. These methods typically compare differences between the reference image (i.e. before) and the current image (after) to detect paste. One drawback of these techniques is that they require relatively significant storage, retrieval and buffer capabilities to accommodate the reference images. Another drawback of these techniques is that they are subject to and are adversely affected by typical variations found between otherwise identical substrates. To avoid this problem, new reference images must be acquired for each substrate to be inspected, but this action can slow the process considerably and may be inappropriate for use in a high speed production environment.

SUMMARY OF THE INVENTION

Embodiments of the present invention perform mathematical operations on a digitized image to separate areas of solder paste texture from other dissimilarly textured (non solder paste) areas on a printed circuit board, stencil, wafer, or substrate.

In general, one aspect of the invention features a method of inspecting a substrate having a substance deposited thereon. The steps of the method include depositing the substance onto the substrate; capturing an image of the substrate; detecting variations in texture in the image to determine a location of the substance on the substrate; and comparing the location of the substance with a desired location.

The method can also include the step of comparing an area of the substrate having the substance with a desired area. The substance may include solder paste.

The method can further include the step of detecting variations in solder paste texture by detecting variations independent of the relative brightness of the non-substance background features on the substrate by dividing the image into pixels, and comparing the brightness levels of each pixel with its pixel neighbors.

In the method, a real-time image may be captured and digitized.

In another aspect of the invention, the step of depositing a substance includes the step of printing a substance onto a substrate using a stencil printer. The method further includes the step of providing a feedback signal to adjust the stencil printer. The stencil printer is adjusted based upon a comparison of the location of the substance with the desired location. The feedback signal may also be used to adjust the stencil printer based upon the comparison of an area of the substance with either a desired or predetermined area.

In another aspect, the invention includes a screen printer that dispenses a viscous material at a predetermined location on a substrate. The screen printer includes: a frame; a material dispenser, coupled to the frame, the material dispenser containing a viscous material to be printed on a substrate; a support apparatus, coupled to the frame, that supports the substrate in a printing position located beneath the material dispenser; a camera having a field of view that includes the substrate in a printing position; and a processor in electrical communication with the camera. The processor being programmed to perform texture based recognition on the viscous material printed on the substrate.

In yet another aspect, the invention includes a system for dispensing solder paste at a predetermined location on a substrate. The system includes a dispenser that dispenses material on the substrate; a controller for maintaining the operations of the dispenser; and a processor. The processor is in electrical communication with the controller. The processor is programmed to perform texture based recognition of a solder paste deposit located on the substrate. The processor also determines the quality of the solder paste deposit, and the contours of the solder paste deposit relative to predetermined locations on the substrate. The processor is part of a control loop that comprises the controller in electrical communication with the dispenser.

In still another aspect, the invention includes an inspection system for detecting the presence and location of a substance on a substrate. The inspection system includes a locator that performs location analysis on various pixels in an image of the substance on the substrate. The inspection system also includes a processor that is in electrical communication with the locator. The processor is programmed to perform texture based recognition of the substance located on the substrate, and to determine the quality of the substance and the contours of the substance relative to predetermined locations on the substrate.

In addition, the processor may further include a locator, a tuner, and a texture segmentation filter. The locator performs location analysis on various pixels in an image. The tuner varies brightness and contrast levels in the image and includes an automatic gain, offset, and an exposure management system. The tuner provides aliasing control based on an effective sampling rate. The texture segmentation filter is in electrical communication with the locator and is used to divide the image into texture regions. The texture segmentation filter includes a sharpening operator, a Laplace operator, and a smoothing operator for further improving image quality. The smoothing operator further includes a mechanism for boosting or enhancing the effect of the texture segmentation filter.

Alternatively, the inspection system may also include a first filter that is in electrical communication with the locator wherein the first filter includes a filter for enhancing the image. The inspection system may further include a tuner in electrical communication with the first filter that has an automatic gain, offset, and exposure management system that varies brightness and contrast levels in the image; and a second filter in communication with the tuner that provides anti-aliasing when the image of the substance on the substrate is magnified beyond the effective sampling rate of the process.

In another aspect of the invention, an option is provided to increase the speed of operation of the inspection system. Specifically, a fill-factor option may be selected to produce only a partially processed image of the substrate to be appropriately interpreted as such in subsequent processes.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIGS. 5A–5C is a representation of various filters typically used in the method of the invention;

DETAILED DESCRIPTION

Figure 1A:
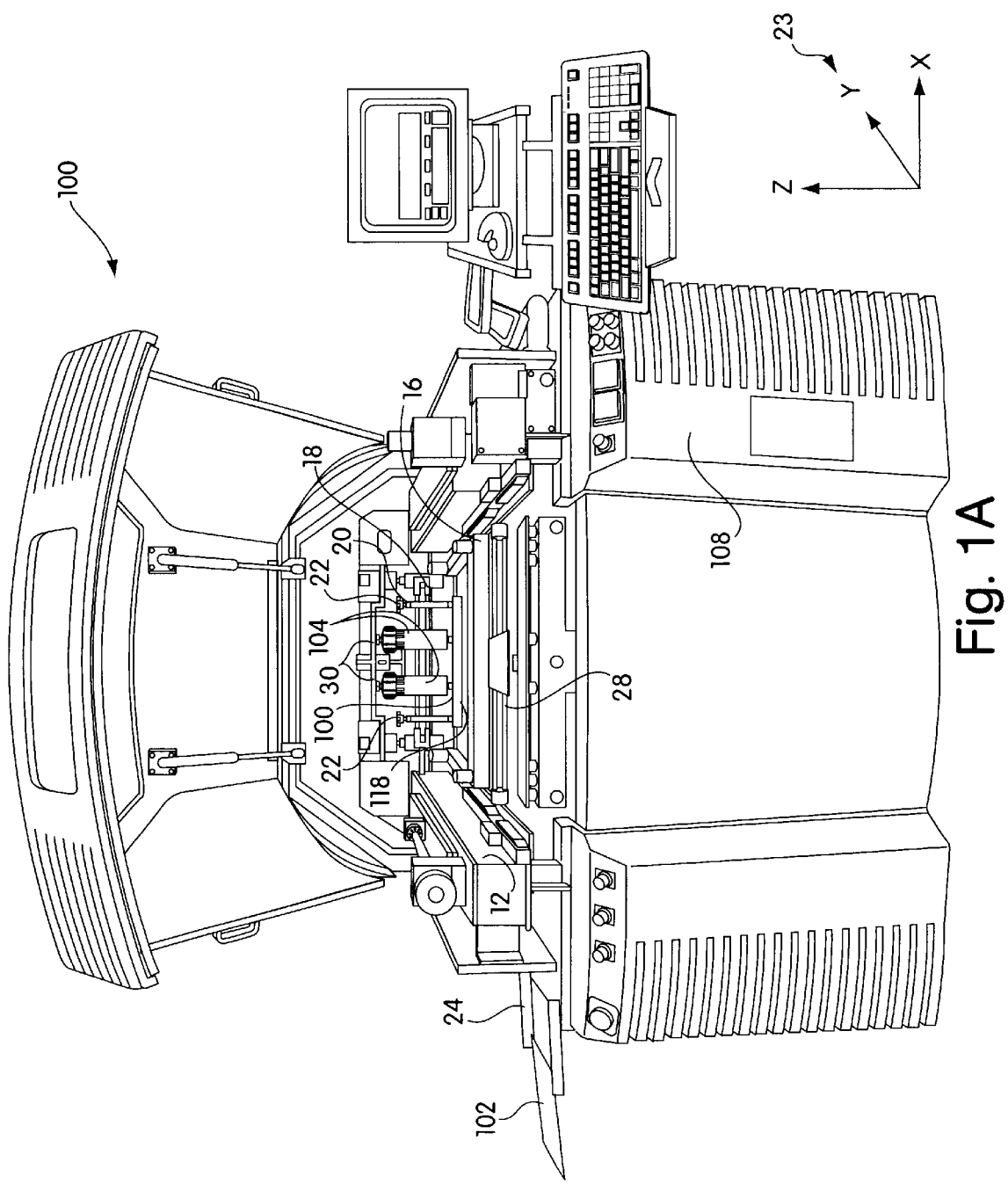
FIG. 1A provides a front view of a stencil printer in accordance with one embodiment of the present invention.

One embodiment of the present invention generally relates to a stencil printer utilizing a method for solder paste texture recognition. FIG. 1A shows a front view of a stencil printer 100 in accordance with one embodiment of the present invention. The stencil printer 100 includes a frame 12 that supports components of the stencil printer including a controller 108, a stencil 16, and a dispensing head 118 having a dispensing slot 118a from which solder paste may be dispensed.

The dispensing head 118 is coupled to a first plate 18 using two thumbscrews 22. The first plate 18 is coupled to a second plate 20 which is coupled to the frame 12 of the stencil printer 10. The first plate 18 is coupled to the second plate 20 in such a manner that the first plate can be moved with respect to the second plate along a z-axis, the z-axis being defined by the coordinate axis system 23 shown in FIG 1A. The first plate is moved by motors under the control of the controller 108.

The second plate 20 is movably coupled to the frame 12 such that the second plate 20 can move with respect to the frame 12 along an x-axis, the x-axis also being defined by the coordinate axis system 23. As described below, the movements of the first and second plates allow the dispensing head 118 to be placed over the stencil 16 and moved across the stencil to allow printing of solder paste onto a circuit board.

Stencil printer 100 also includes a conveyor system having rails 24 for transporting a circuit board 102 to a printing position in the stencil printer. The stencil printer has a number of pins 28, positioned beneath the circuit board when the circuit board is in the dispensing position. The pins are used to raise the circuit board 102 off of the rails 24 to place the circuit board in contact with, or in close proximity to, the stencil 16 when printing is to occur.

The dispensing head 118 is configured to receive two standard SEMCO three ounce or six ounce solder paste cartridges 104 that provide solder paste to the dispensing head 118 during a printing operation. Each of the solder paste cartridges 104 is coupled to one end of a pneumatic air hose 30. As readily understood by those skilled in the art, the dispensing head could be adapted to receive other standard, or non-standard, cartridges. The other end of each of the pneumatic air hoses is attached to a compressor that under the control of the controller 108 provides pressurized air to the cartridges to force solder paste to flow from the cartridges into the dispense head 118 and onto the screen 16. Mechanical devices, such as a piston, may be used in addition to, or in place of, air pressure to force the solder paste from the SEMCO cartridges into the dispensing head.

In one embodiment of the present invention, the controller 108 is implemented using a personal computer using the Microsoft DOS or Windows® NT operating system with application specific software to control the operation of the stencil printer as described herein.

The stencil printer 100 operates as follows. A circuit board 102 is loaded into the stencil printer using the conveyor rails 24. A machine vision process for automatically aligning the printed circuit board 102 to stencil 16 is implemented. The printed circuit board 102 and stencil 16 are brought into contact, or nearly so, prior to application of the solder paste. The dispensing head 118 is then lowered in the z-direction until it is in contact with the stencil 16. Pressurized air is provided to the cartridges 104 while the dispensing head is moved in the x direction across the stencil 16. The pressurized air forces solder paste out the cartridges and creates pressure on the solder paste in the dispensing head forcing solder paste from the dispensing slot 118a of the dispensing head 118 through apertures in the stencil 16 and onto the circuit board 102. Once the dispensing head 118 has fully traversed the stencil 16, the circuit board 102 is lowered back onto the conveyor rails 24 and transported from the printer so that a second circuit board may be loaded into the printer. To print on the second circuit board 102, the dispensing head 118 is moved across the stencil in the direction opposite to that used for the first circuit board. Alternatively, a squeegee arm could swing in to contain the solder paste in the dispenser, and the dispenser can then be lifted in the z-direction and moved back to its original position to prepare to print on the second circuit board using a similar direction stroke.

As described further in U.S. patent application Ser. No. 09/235,034 entitled "Method and Apparatus for Dispensing Material in a Printer" filed on Jan. 21, 1999, assigned to Speedline Technologies, Inc., the assignee of the present invention and incorporated herein by reference, the dispensing head 118 is lowered into a printing position so that it is in contact with the stencil. The stencil printer 100 operates by forcing solder paste from the dispensing head 118 onto the stencil using air pressure applied to each of the SEMCO cartridges as the dispensing head moves across the stencil. In the printing position, two blades (not shown) come into contact with the top surface of the stencil. For each direction that the dispensing head moves across the stencil, one of the blades will be a trailing blade and will scrape any excess solder paste off the stencil.

At the conclusion of printing, when it is desired to lift the dispensing head 118 off of the stencil, the controller 108 turns off the pressurized air source, prior to lifting the dispensing head 118. This causes the solder paste to remain in a chamber (not shown) when the dispensing head 118 is lifted and effectively reduces the amount of solder paste that is left on the stencil when printing is complete.

After the solder paste has been deposited onto the printed circuit board, a machine vision process for automatically inspecting the printed circuit board is implemented. In one embodiment of the present invention, the inspection process uses a texture recognition method to determine whether solder paste has been properly deposited onto predetermined contact regions located on the printed circuit board. The solder paste texture recognition system used in embodiments of the present invention will now be described.

Figure 1B:
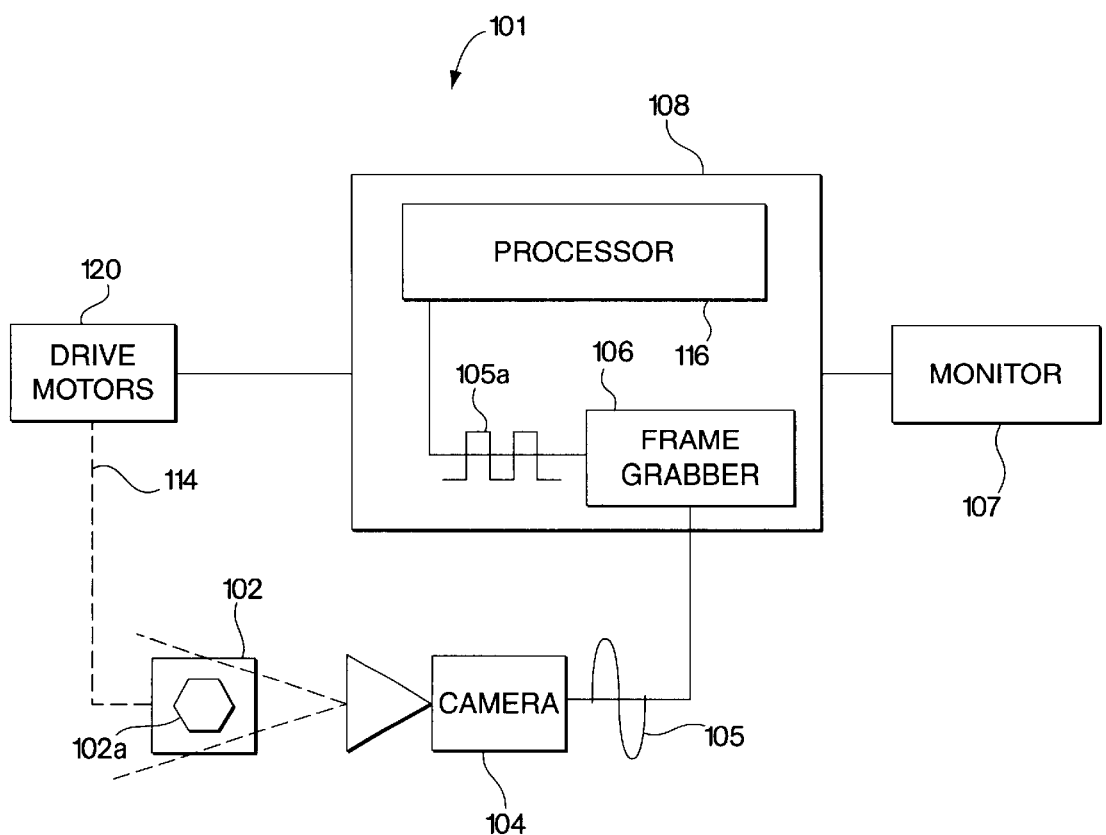
FIG. 1B is a schematic of another embodiment of the present invention.

Referring to FIG. 1B, a functional block diagram 101 of the screen printer 100 is shown. In FIG. 1B, the screen printer 100 is shown inspecting a substrate 102 having a substance 102a deposited thereon. In one embodiment, the substrate 102 includes a printed circuit board, stencil, wafer, or any flat surface, and the substance 102a includes solder paste.

Figure 2A:
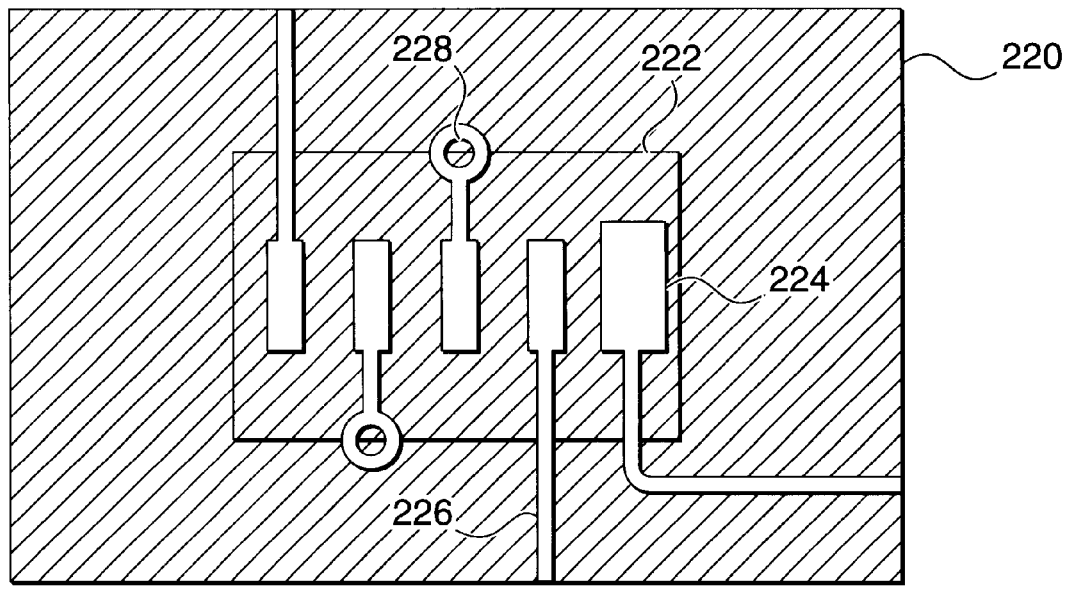
FIGS. 2A–2B is a schematic of a printed circuit board.
Figure 2B:
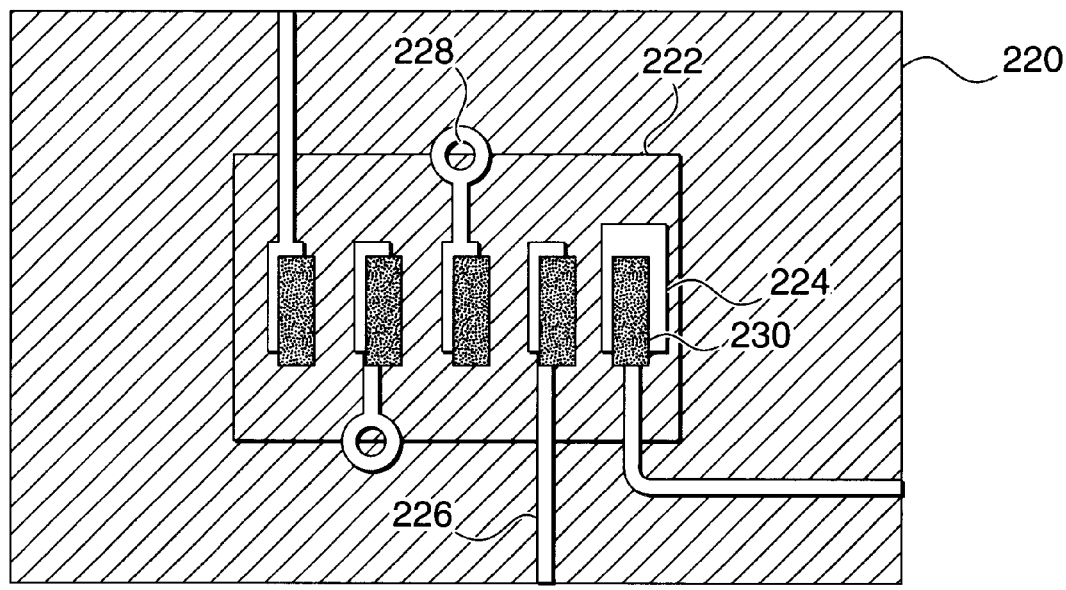

FIG. 2A and FIG. 2B, show a top plan view of a printed circuit board 220 which may be used in place of the substrate 102 in FIG. 1B. The printed circuit board 220 has a region of interest 222 and contact regions 224. It also has traces 226 and vias 228. FIG. 2A shows the printed circuit board 220 without solder paste deposits on any of the contact regions 224. FIG. 2B shows solder paste deposits 228 distributed on the predetermined contact regions 224 of the printed circuit board 220. In the printed circuit board 220, the predetermined areas 224 are distributed across a designated region of interest 222 of the printed circuit board 220.

FIG. 2B shows a misalignment of the solder paste deposits 230 with contact pads 224. Each of the solder paste deposits 230 is partially touching one of the contact regions. However, to insure good electrical contact and prevent bridging between pad regions (i.e. short circuits), solder paste deposits 230 should be aligned to contact pad regions 224 within specific tolerances. The invention described herein discloses a method using texture recognition to detect misaligned solder paste deposit on contact pads, and as a result, generally improves the manufacturing yield of printed circuit boards.

Again referring to FIG. 1B, in one embodiment of the present invention, a method for solder paste texture recognition includes a step of using a camera 104 to capture an image of the substrate 102 having a substance 102a deposited thereon. In one embodiment, the camera 104 is a charge coupled device that transmits a real-time analog signal 105 to a frame grabber 106. The real-time analog signal corresponds to an image of the substrate 102 having the substance 102a deposited thereon. The camera 104 may obtain an image of the substance 102a using a raster type scan, or an area scan of the substrate 102. In one embodiment, the camera 104 is also able to image the bottom side of the substrate 102 or stencil 16 by using a combination of mirrors, beam splitters, or another camera.

The camera 104 transmits an analog signal 105 to a frame grabber 106. The analog signal 105 contains information regarding the image of the substrate 102 and the substance 102a deposited thereon. The frame grabber 106 digitizes the analog signal 105 and creates a digitized image 105a which may be displayed on a monitor 107. The digitized image 105a is divided into a predetermined number of pixels, each having a brightness value from 0 to 255 gray levels (in an 8-bit range). In one embodiment of the invention, the analog signal 105 represents a real-time image signal of the substrate 102 and substance 102a deposited thereon. However, in an alternative embodiment, a stored image is transmitted from a memory device coupled to a controller 108. Furthermore, depending upon the camera 104, and other devices used to acquire the image of the substrate 102 and the substance 102a, the brightness values used could range from 0 to 65,535 gray levels (in a 16-bit range).

The frame grabber 106 is electrically connected to the processor 116. The controller 108 includes a processor 116 and the frame grabber 106. The processor 116 calculates statistical variations in texture in the image 105a of the substance 102a. The texture variations in the image 105a of the substance 102a are calculated independent of relative brightness of non-substance background features on the substrate 102, so that the processor 116 can determine the location of the substance 102a on the substrate 102, and to compare the location of the substance 102a with a desired location. In one embodiment of the present invention, if the comparison between the desired location and the actual location of the substance 102a reveals misalignment exceeding a predefined threshold, the processor 116 responds with adaptive measures to reduce or eliminate the error, and may reject the substrate or trigger an alarm via the controller 108. The controller 108 is electrically connected to the drive motors 120 of the stencil printer 100 to facilitate alignment of the stencil and substrate as well as other motion related to the printing process.

The controller 108 is part of a control loop 114 that includes the drive motors 120 of the stencil printer 100, the camera 104, the frame grabber 106, and the processor 116. The controller 108 sends a signal to adjust the alignment of a stencil printer frame 12, and thus the mechanically coupled stencil 16, should the substance 102a on the substrate 102 be misaligned.

Figure 3:
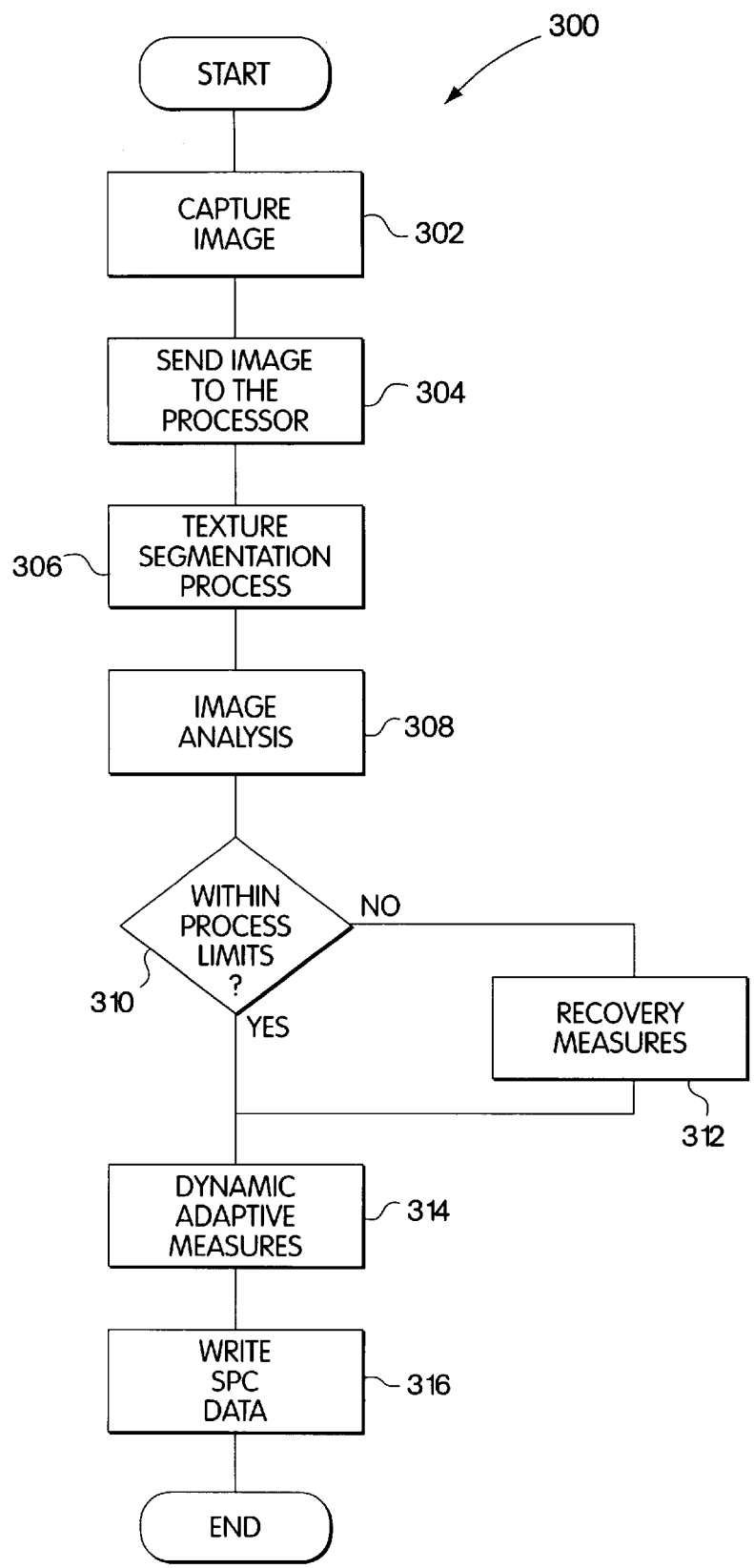
FIG. 3 is a flowchart of the method for inspecting solder paste deposits on a substrate.

FIG. 3 shows a flowchart 300 of the method for inspecting solder paste deposits on a substrate. Step 302 includes capturing an image 105 of a substance deposited onto a substrate 102. In one embodiment, the substance 102a is solder paste and the substrate 102 is a printed circuit board. The image 105a of the substrate 102 with a substance 102a deposited thereon may be captured in real-time or retrieved from a computer memory. Step 304 includes sending the image 105a to a processor 116. The remaining steps in the inspection method are performed by the processor 116. Step 306 detects texture variations in the image 105a utilizing various texture sensitive operators described below. The texture variations are used to determine the location of the substance 102a on the substrate 102. In Step 308, the processor 116 is programmed to compare the texture variations at a particular location with texture features at predetermined locations of the substrate. In Step 310, if the variations are within predetermined limits, the processor 116 may respond with dynamic adaptive measures (Step 314) to refine the main process. If the variations lie outside predetermined limits, then Step 314 triggers appropriate recovery measures through Step 312 to reject the substrate, terminate the process, or trigger an alarm via controller 108. Related statistical process control (SPC) data are recorded in step 316 along with other process data and is available for review and analysis both locally and via network access.

As mentioned above, detecting the variations of texture in the image 105a, and comparing the location and area of the substance 102a with a predetermined location and area, utilizes a processor 116.

Processor functions

The technique used by the processor 116 to recognize solder paste 228 on a printed circuit board 224 will now be described. In one embodiment of the present invention, the processor 116 performs four functions. The four functions are image enhancement, texture segmentation, image location analysis, and process control.

As previously stated, existing solder paste inspection systems primarily use basic single or dual thresholding methods that only utilize differences in pixel brightness of the original image to identify solder paste. In embodiments of the invention, the processor 116 also utilizes single and dual thresholding techniques but on an image that is preprocessed using various texture sensitive operators such that single and dual thresholds may be used to separate specific regions based on relative texture, as in this case, to identify the location and area of solder paste deposits. The dual threshold technique is preferred since it provides a more accurate scalable transition at edge pixels or any region of uncertainty in the texture based image.

The texture sensitive operators utilized by the method of the invention include a sharpening operator, a Laplacian operator, and a smoothing operator that includes a boosting mechanism. Each of the operators will be described as part of the processor functions.

Texture is a variation of brightness. In particular, texture refers to the local variation in brightness from one pixel to another. Thus, if brightness is interpreted as the elevation in an image, then the texture is a measure of surface roughness.

In one embodiment of the present invention, a range operator may be used to detect texture in image 105a. The range operator represents the difference between maximum and minimum brightness values in a neighborhood. The range operator converts the original image 105a to one in which brightness represents the texture. Specifically, the original brightness features disappear and different structural regions are distinguished by the range brightness. The range operator may also be used to define edge boundaries of an image.

Another texture operator is represented by the variance in neighborhood regions. In one embodiment of the invention, the processor is programmed to calculate the variance. The variance is essentially the sum of squares of the difference between the brightness of a central pixel and its neighbors. If the sum of squares is first normalized by dividing by the number of pixels in the neighborhood, then this result represents the root mean square (RMS) difference of values and corresponds to the surface roughness. These texture sensitive operators and methods may be implemented using rudimentary tools provided by software suppliers to effectuate machine vision processes. These processes are generally discussed by John C. Russ in "The Image Processing Handbook, Second Edition", and in the "Handbook of Computer Vision Algorithms in Image Algebra", by Gerhard X. Ritter and Joseph N. Wilson which are incorporated herein by reference.

Figure 4A:
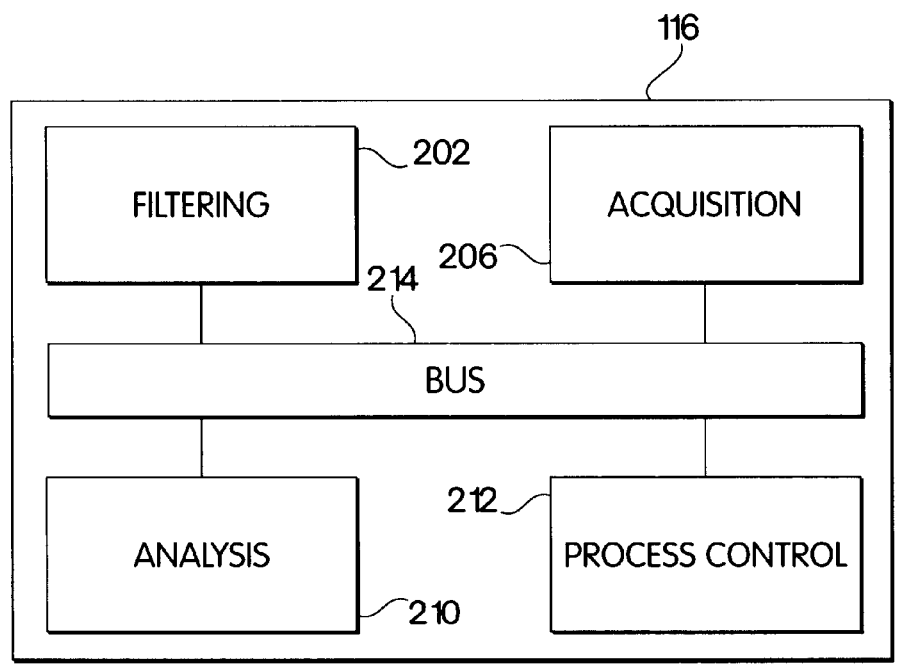
FIGS. 4A–4B is a schematic of various regions within a processor that utilizes the method of the invention.

In one embodiment of the invention, the processor 116 is programmed to perform separate functions using the aforementioned texture sensitive operators. The operations performed by the processor 116 are logically represented in a functional block diagram shown in FIG. 4A, wherein the separate operations are shown connected by an information bus 214 which facilitates sharing data between the functional blocks. The filtering section 202 of the processor 116 performs a texture segmentation process. The acquisition section 206 of the processor 116 calculates the gain and offset required to provide a specific contrast and brightness to enhance a run-time image 105a. The analysis section 210 of the processor 116 performs location and contour analysis of the solder paste region 102a on the substrate 102 and compares both to predetermined parameters. The process control section 212 of the processor 116 is used to minimize any aliasing in an image of the solder paste region 102a. The following is a discussion of the performance of each of the various functions of the processor 116.

The Filtering Section 202

Figure 4B:
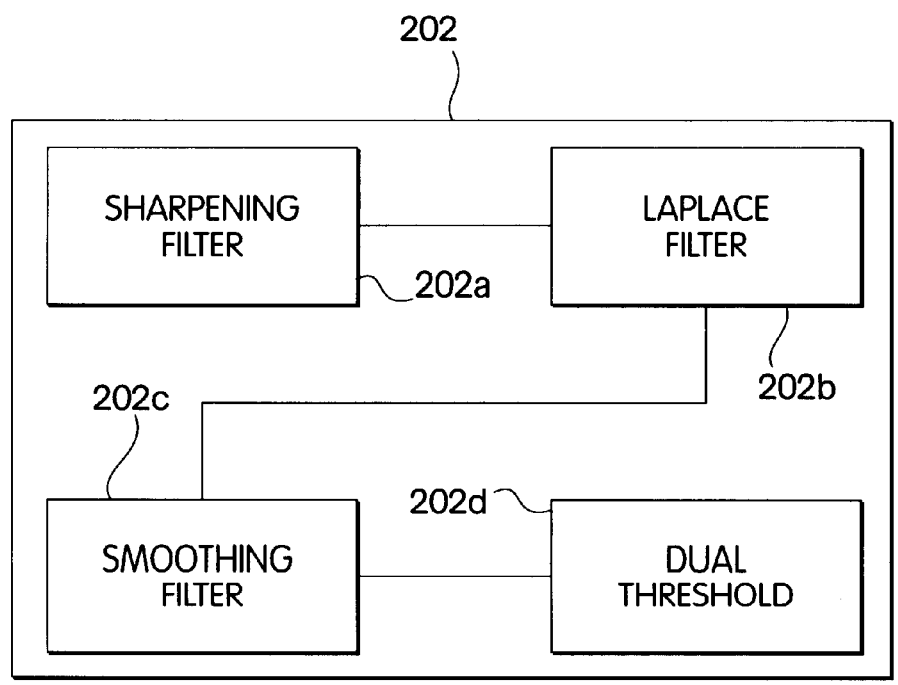

In one embodiment of the invention, the filtering section 202 of the processor 116 performs image filtering utilizing a Laplacian filter 202B shown in FIG. 4B. The Laplacian filter 202B includes Laplacian operators. The Laplacian operator is essentially an approximation to the linear second derivative of brightness. The operator highlights the points, lines and edges of an image and suppresses uniform and smoothly varying regions of the image. In one embodiment, the Laplacian operator is represented by the 3 by 3 matrix shown in FIG. 5A. The 3 by 3 matrix, referred to as a kernel, has a central pixel having a value equal to negative four which means that the brightness value of the central pixel in the image 105a is multiplied by negative four. In the Laplacian kernel, the values of the four neighbors touching the sides, above and below the central pixel is equal to one. Accordingly, the brightness levels of the four nearest neighbors to the central pixel in the image 105a are multiplied by one. Typically, the four neighbors are located using the directions north, east, south and west relative to the central pixel. However, other orientations are possible (as shown in FIGS. 8A–8H).

The specified pixels of the kernel are multiplied by the corresponding kernel coefficient and then added together. Note that, in this embodiment, the total sum of the Laplacian kernel coefficients equals zero. Consequently in a region of the image 105a that is uniform in brightness, or has a uniform gradient of brightness, the result of applying this kernel reduces the gray level to zero. However, when a discontinuity is present, e.g., a point, line or edge, the result of the Laplacian kernel may be non-zero depending upon where the central point lies on the discontinuity.

Because the image 105a can be divided into millions of pixels, and a method of the invention compares each pixel with its neighbors, processor speed may be effected. However, in an embodiment of the invention, an option is provided to increase the speed of operation of the inspection system by reducing the time to capture and process an image. Specifically, a fill-factor option may be selected to produce only a partially processed image of the substrate 102. The fill-factor is a multiplier that may be used with a subsequent blob-type operator to arrive at a calculated equivalent area of the image of the substrate 102.

The image filtering method performed by the filtering section 202 further includes a sharpening step. The sharpening step is implemented by a sharpening filter 202A shown in FIG. 4B. The sharpening filter 202A improves the image 105a by locally increasing the contrast at areas of discontinuity. The sharpening filter can be described as a specific type of Laplacian filter. As mentioned, the Laplacian operator is an approximation to the linear second derivative of the brightness (B) in directions x and y, and is represented by the equation:

$$\nabla^2 B \equiv \partial^2 B/\partial x^2 + \partial^2 B/\partial y^2. \qquad (1.0)$$

The above equation (1.0) is invariant to rotation, and hence insensitive to the direction in which the discontinuity runs. The effect of the Laplacian operator is to highlight the points, lines and edges in an image 105a and to suppress uniform and smoothly varying regions. By itself, this Laplacian image is not very easy to interpret. However, by combining the Laplacian enhancements with the original image 105a, the overall gray scale variation is restored. This technique also sharpens the image by increasing the contrast at the discontinuities.

Figures 5A, 5B, 5C:
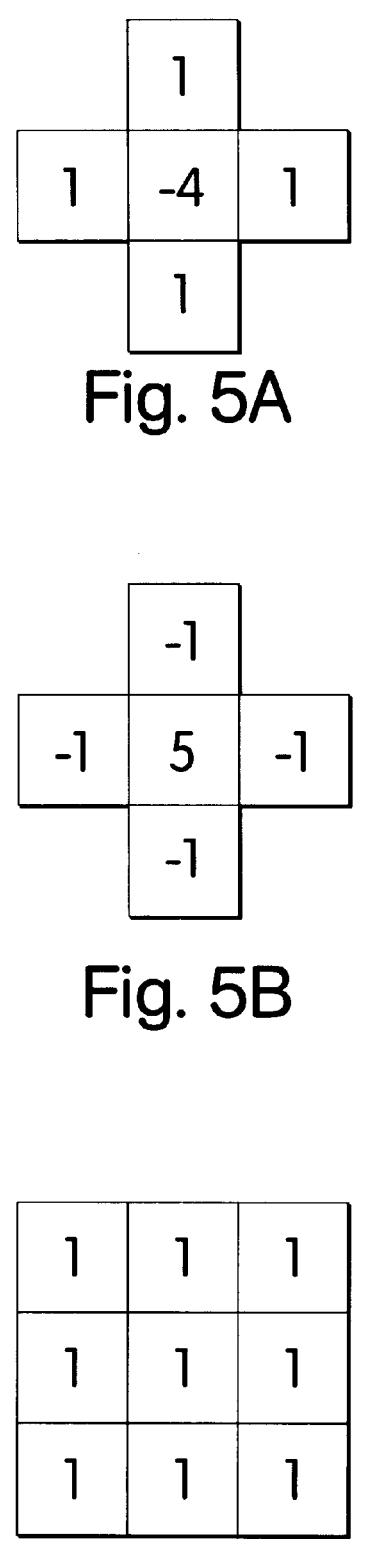

The sharpening kernel of the sharpening filter 202A used in one embodiment of the invention to locally increase the contrast is shown in FIG. 5B. Note that the central weight of the sharpening kernel has a value of five. In another embodiment of the invention, the central weight is negative five, and the north, east, south and west neighbors are multiplied by one.

The sharpening kernel, also referred to as a sharpening operator, improves the contrast produced at the edges of the image 105a. Justification for the procedure can be found in two different explanations. First, the blur in an image can be modeled as a diffusion process which obeys the partial differential equation:

$$\partial f/\partial t = \kappa \nabla^2 f, \qquad (1.2)$$

where the blur function is $f(x,y,t)$, t is time and $\kappa$ is a constant. If equation (1.2) is approximated using a Taylor series expansion around time $\tau$, then one can express the brightness of the unblurred image as $$B(x,y) = f(x,y,t) - \tau \partial f/\partial t + 0.5\tau^2 \partial^2 f/\partial t^2 - \ldots \qquad (1.4)$$

If the higher order terms are ignored, then equation (1.4) becomes $$B = f - \kappa \nabla^2 f. \qquad (1.6)$$

Accordingly, the brightness of the unblurred image B can be restored by subtracting the Laplacian (times a constant) from the blurred image $f$.

A second justification for the procedure can be found using Fourier analysis to describe the operation of the Laplacian operator as a high pass filter comprising high and low frequency components of the image brightness. In this approach, a smoothing kernel is described as a low pass filter. This low pass filter removes the high frequency variability associated with noise which can cause the nearby pixels to vary in brightness. Conversely, a high pass filter allows these high frequencies to remain (pass through the filter) while removing the low frequencies corresponding to the gradual overall variation in brightness.

Accordingly, the image filtering method performed by the filtering section 202 of the processor 116 includes a smoothing step. The smoothing step is implemented using a smoothing filter 202C shown in FIG. 4B. The smoothing filter 202C is used to reduce the signal to noise ratio associated with the image 105a. Essentially, the smoothing step performs spatial averaging. The spatial averaging adds together the pixel brightness values in each small region of the image 105a, and divides by the number of pixels in the neighborhood, and uses the resulting value to construct a new image.

In one embodiment of the invention, the smoothing operator utilized is shown in FIG. 5C. In this embodiment, the value of the central and neighboring pixels in the smoothing kernel are all equal to one. Smoothing is used here to average similarly textured regions to be separated via subsequent thresholding operations.

Smoothing operations tend to reduce the maximum values and increase minimum values in the image. Depending on the ratio of bright pixels versus dark pixels, the resulting image may brighten or darken as smoothing is applied. Performing an unlimited number of smoothing operations would ultimately result in an image with only one gray level. In this embodiment dark pixels (indicating low frequencies) are more prevalent, so instead of dividing by nine, the number of pixels used, the sum is divided by eight to effectively boost the smoothed image by a factor of 1.125 after each application or pass such that contrast and brightness is improved for subsequent thresholding operations. This also improves processing speed by allowing a relatively faster shift-by-3 (binary) operation rather than a numerically equivalent but slower division by eight. In this embodiment, the best results are typically observed after six smoothing applications, or passes, as described above.

In another embodiment of the invention, one may reduce the signal to noise ratio by performing a kernel operation. The kernel operation is spatial averaging that is performed by replacing each of the pixels with the average of itself and its neighbors. In one embodiment of the invention, a computer program performs the kernel operation and calculates the above described image morphologies using sharpening operators, Laplacian operators, and smoothing operators.

The Acquisition Section 206

In one embodiment of the invention, the processor 116 includes an acquisition section 206 that provides automatic gain and offsets (AGO) used to view or capture the image 105a. In general, any means to adjust or otherwise enhance brightness, contrast or overall quality of the real-time image 105 or stored image 105a, or portions of the image 105a may be applied. Such enhancements may include, but are not limited to, lighting configurations, utilizing optical filters, spatial filters, polarizers, or any method that includes a combination thereof. The enhancements may further include software manipulation of the pixels in the image 105a to provide optical corrections to aberrations, vignetting and lighting.

Figure 6:
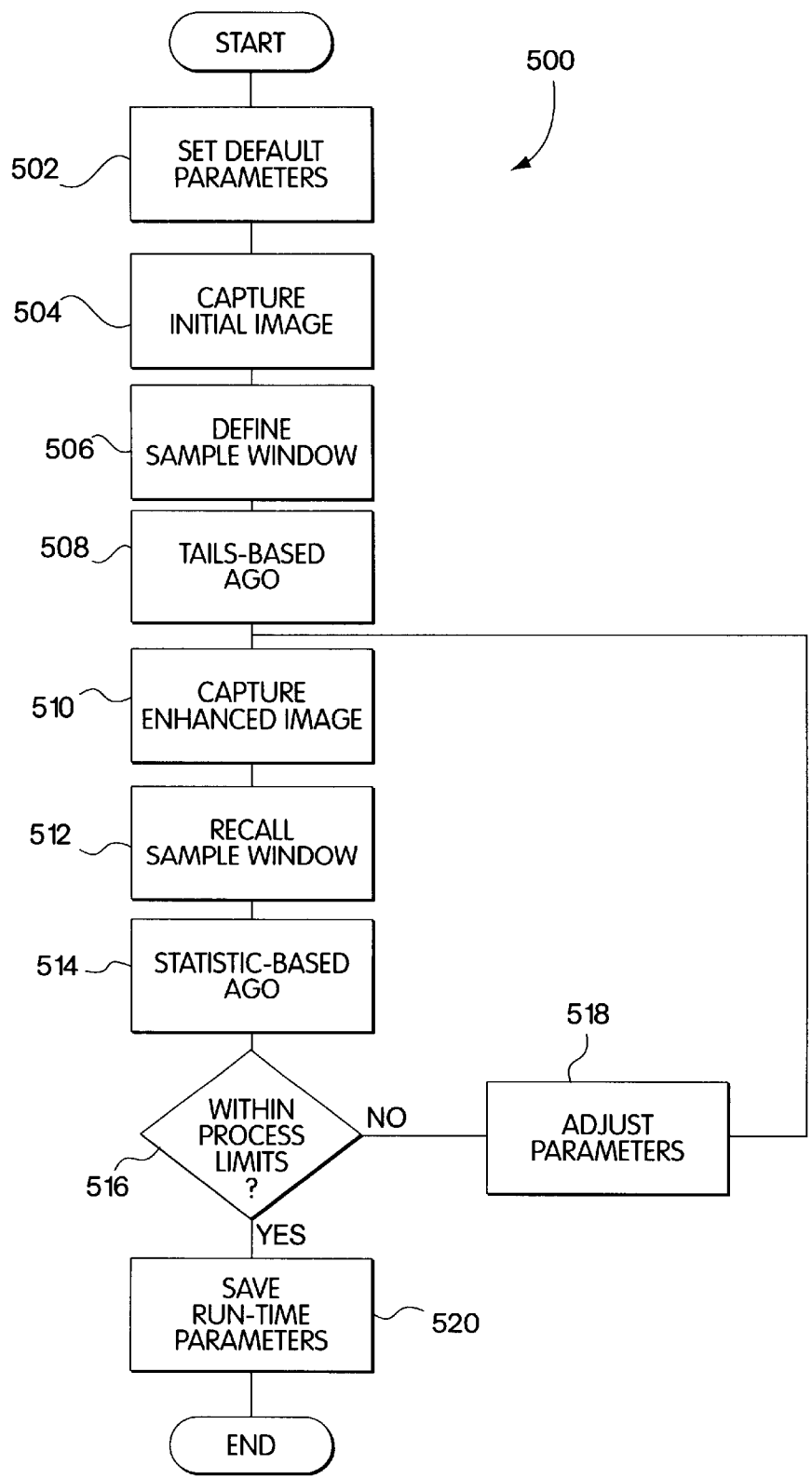
FIG. 6 is a flowchart of a method that implements an automatic gain offset feature of the invention.

FIG. 6 shows a flowchart 500 that describes the acquisition section 206 of the processor 116 in one embodiment of the invention. The steps described by the flowchart 500 may be implemented by software in the processor 116, hardware components, or a combination of hardware and software. Referring to FIG. 6, system parameters may be set manually or automatically in step 502, where the system default parameters may include the type of camera 104 being used, and the input voltages to various tail locations. Tail locations refer to the left (darkest) and right (brightest) ends, or tails, of a brightness histogram of the image 105a.

Step 504 captures the initial image 105, and a sampling window for analyzing the image is defined in Step 506. The sampling window may be manually or automatically defined and is the source of image data for the calculations performed in steps 508 and 514. Step 508 calculates the gain and offset required to move the left and right tails of the image 105a to predetermined locations. Step 510 performs a second acquisition based on information calculated in step 508 to adjust and enhance the histogram distribution of image data for subsequent operations. In one embodiment of the invention, Step 510 also performs a linear expansion and shift to further improve the image brightness and contrast of image 105a.

In one embodiment of the invention, experimental results indicate that initial limitations may be set as shown in Tables 1 and 2 below when using a video frame grabber equipped with a typical programmable Analog to Digital Converter (ADC):

TABLE 1

Initial ADC command values for the Automatic Gain and Offset function.

| Parameter | Offset | Gain |
| --- | --- | --- |
| Initial Command Values | 16 (for 7.5 IRE = 0) | 127 (for 100 IRE = 255) |

Table 1 shows the initial 8-bit ADC command values that typically allow the full range of standard video input levels, when digitized, to fully span the 8-bit ADC output range without clipping. Note that for a gray scale range from 0 (or 7.5 IRE) to 255 (or 100 IRE) where 100 IRE equals 0.714 volts, the initial command values for the offset and gain is 16 and 127 respectively.

Table 2 below shows the maximum and minimum range of command values used to control an input section of the ADC hardware. Also shown are adjustment limitations based on the typical signal-to-noise performance of the incoming video signal and the expected signal range.

TABLE 2

ADC command value range and limits for the Automatic Gain and Offset function.

| Parameter | Minimum | Maximum |
| --- | --- | --- |
| Command Value Range | 0 | 255 |
| Gain Adjustment Limits | 40 (maximum gain) | 255 (minimum gain) |
| Offset Adjustment Limits | 0 (brightest offset) | 150 (darkest offset) |

Table 3 below shows typical target tail locations used by the Automatic Gain and Offset (AGO) function to determine ADC gain and offset command values that, when applied in subsequent acquisitions, tend to limit the tails of similar regions or features of interest to the target values.

TABLE 3

Initial Target Parameters for the Automatic Gain and Offset function.

| Parameter | Left Tail | Right Tail |
| --- | --- | --- |
| Target Tail Locations for Paste Sample Window | 63 (darkest paste feature) | 191 (brightest paste feature) |
| Target Tail Locations for Full Field of View | 15 (darkest feature) | 240 (brightest feature) |

In general, the target values are selected that optimize regions or features of interest for a specific image processing task. In Step 508, tail locations 63 and 191 shown in Table 3 are used by the AGO function to enhance solder paste regions without regard to the validity of other non-paste image data. Alternatively, the tail locations 15 and 240 shown in Table 3 may be used to provide a full field of valid image data and to allow tails of subsequent acquisitions to drift slightly without loss due to clipping at each end of the 8-bit gray scale.

In one embodiment of the invention, Step 508 includes clip range detection, warning, and corrective methods for RS170/NTSC signal voltages that exceed approximately 120±3 IRE, or 0.835 to 0.878 volts. Processor 116 automatically adjusts acquisition parameters such that signal voltages remain within normal operating range.

Typical RS170/NTSC cameras have output signal clip levels set to 120±3 IRE, or approximately 0.835 to 0.878 volts, where 100 IRE equals 0.714 volts. If the voltages are over the clip range, a warning message is sent indicating that saturation has either occurred or is likely. If the voltages are below the clip range, then the method proceeds to Step 510. Step 510 administers the newly calculated parameters to acquire an enhanced image 105a for further processing. Step 512 recalls the sample window coordinates defined in Step 506 and applies them to the new image captured in Step 510. Step 514 performs a statistics-based AGO function on the new sample window to determine optimal run-time acquisition and processing parameters. This method of the invention insures that similar statistical characteristics are produced in paste regions of images that are acquired at run-time.

In Step 516, the method of the invention determines whether the preliminary run-time acquisition parameters are within predetermined hardware and software limits. Also determined in Step 516 is whether processing parameters, including kernel geometry and the effective sampling rate, are optimized to provide the maximum level of performance. If not, then the appropriate system parameters are adjusted in Step 518, and new parameters are inserted at Step 510. Steps 510 through 516 are then repeated. Once the run-time parameters are determined they are saved in memory at Step 520 and the method of the invention terminates.

Figure 7A:
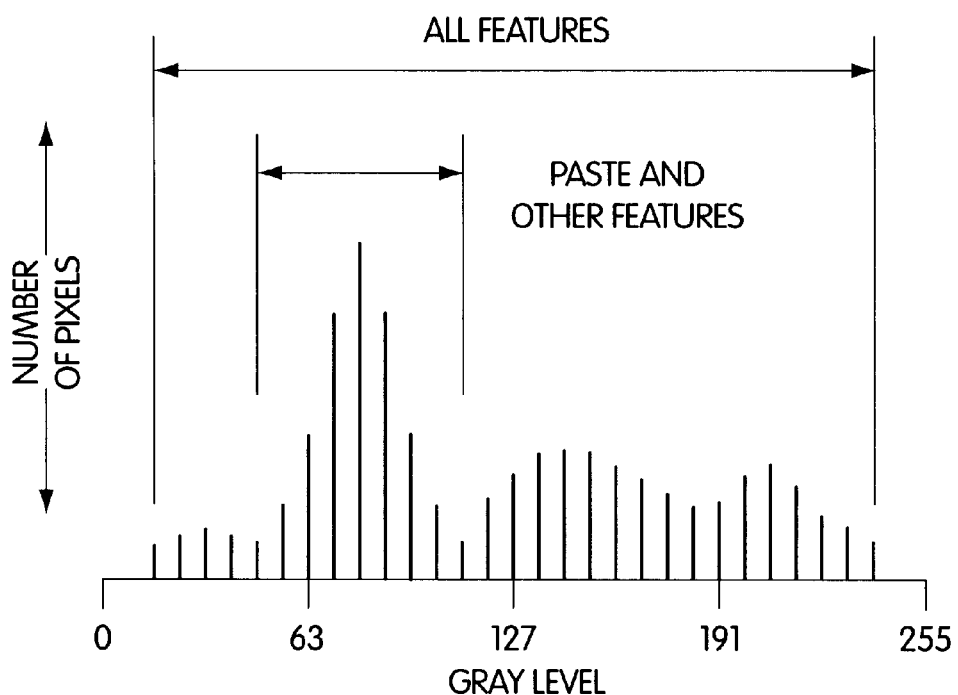
FIGS. 7A–7B is a schematic representation of solder paste distributions on a printed circuit board.
Figure 7B:
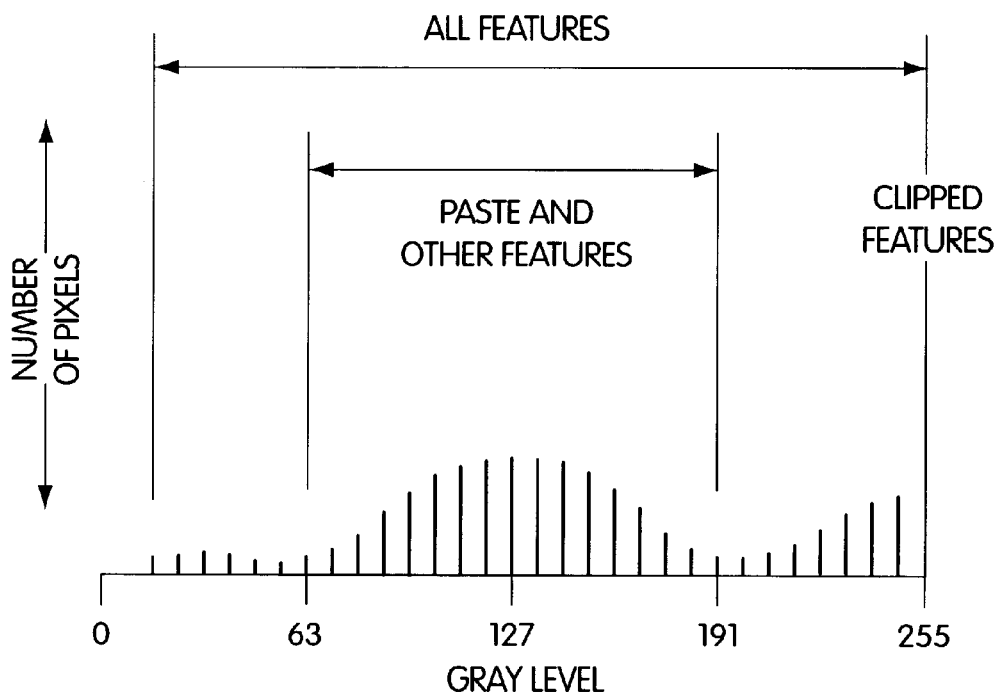
Figure 8A:
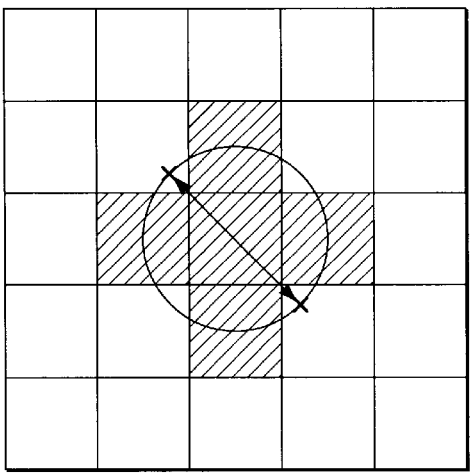
FIGS. 8A–8H is a schematic of various kernel configuration options for paste texture spacing versus magnification.
Figure 8B:
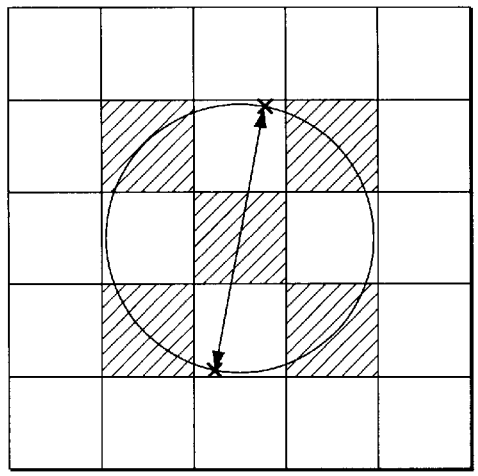
Figure 8C:
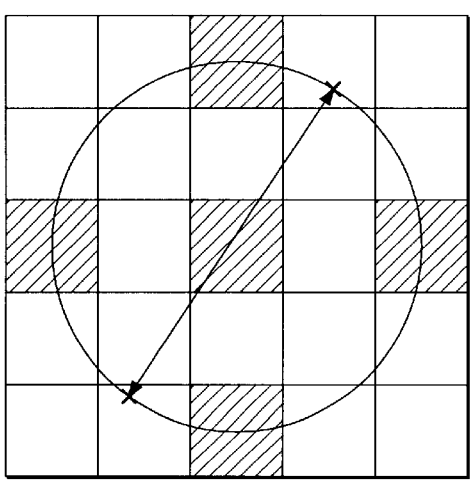
Figure 8D:
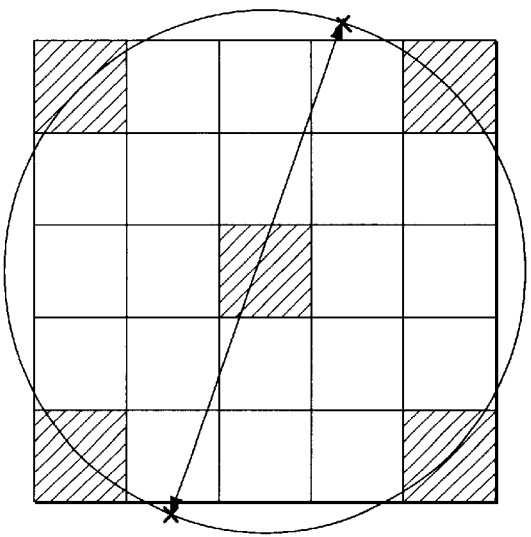
Figure 8E:
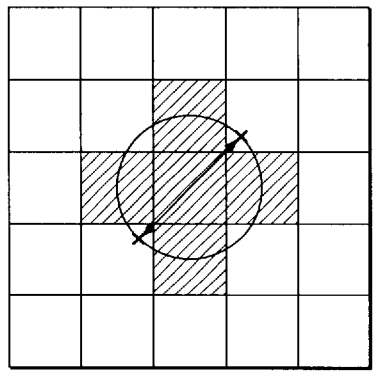
Figure 8F:
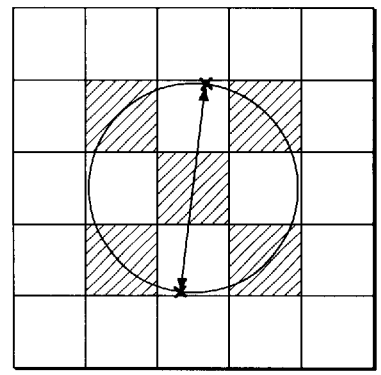
Figure 8G:
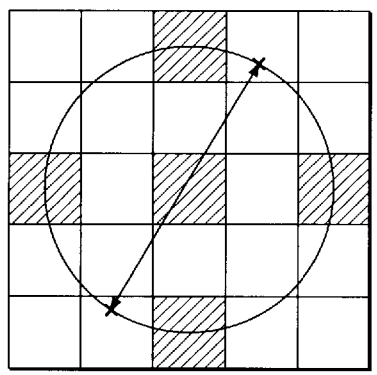
Figure 8H:
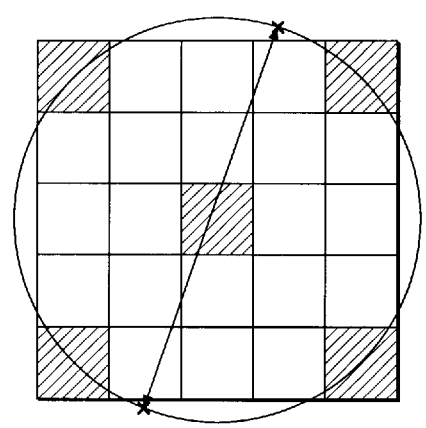

A histogram that shows the effects of the AGO in section 206 of the processor 116 is shown in FIGS. 7A–7B. Referring to FIG. 7A, a histogram of the original image of a printed circuit board 220 having solder paste 102 deposited thereon is shown. The x-axis of the histogram represents the gray levels from 0 to 255, and the y-axis represents the number of image pixels at each gray level. FIG. 7B shows a histogram of the same image with paste contrast enhanced. FIG. 7B also shows a considerable number of non-paste pixels clipped at 255. In one embodiment of the invention, the left tail of the original image equals fifteen, and the right tail equals 240 on a gray scale level that extends from 0 to 255 (implying an 8-bit gray scale). In another embodiment of the invention, Step 502 allows the processor 116 to automatically calculate and set initial acquisition parameters, or alternatively allows an operator to set the parameters.

As mentioned, Step 510 acquires a new image 105a to enhance the region of interest, in this case solder paste, based on parameters calculated in Step 508. In one embodiment of the invention and referring to FIG. 7B, the gray levels for the left tail and right tail of the enhanced image 105a occur at 15 and 255. The calculation performed by the acquisition section 206 of the processor 116 produces a linear expansion and shift of the solder paste region such that the solder paste region of interest occurs between tails 63 and 191. FIG. 7B also shows an increased number of pixels at gray level 255 due to clipping of values that would otherwise exceed 255 when the parameters calculated in step 508 are applied.

Comparing FIG. 7A and FIG. 7B, a reduction in height of the y-axis in areas designated as paste reflects the redistribution of an equal number of paste pixels over more gray levels.

Analysis Section 210

The locator analysis section 210 of the processor 116 is used to determine the location of solder paste relative to the predetermined contact regions 224. Coordinates of each area may be determined using centroids, blob techniques, correlation, and a variety of other search tools. The process of utilizing blob techniques and centroids is well known and discussed by John C. Russ in "The Image Processing Handbook, Second Edition"; pages 416–431, 487–545, and in the "Handbook of Computer Vision Algorithms in Image Algebra", by Gerhard X. Ritter and Joseph N. Wilson; pages 161–172 which are incorporated herein by reference.

The results of the location analysis are used to detect the presence, absence, and alignment of the paste, and thus alignment of the stencil 16 with the desired contact regions 224. Results also provide the basis for other adaptive and corrective process control measures. In one embodiment of the invention, information provided by the locator section 210 is used to modify operational parameters of the dispenser head 118.

Anti-Aliasing of the Solder Paste Image (Process Control Section 212)

The process control section 212 of the processor 116 is used to minimize any aliasing in an image of the solder paste region 102a. In obtaining a digitized image 105a of the solder paste region 102a deposited on a substrate 102, several conditions unique to solder paste texture recognition are considered. Specifically, in one embodiment of the invention, the grain size of the paste and its effect on the quality of the image 105a at various magnifications. Ordinarily, as long as the sampling rate is above the Nyquist frequency aliasing may be averted. However, when imaging solder paste regions, aliasing can also occur without the proper relationships between grain size, focal length, magnification, and the CCD pixel spacing. In one embodiment, the texture recognition method of the invention considers four types of solder paste shown in Table 4 below.

TABLE 4

The types of solder paste used and the various grain sizes.

| Solder Paste | Nominal Grain Diameter | |
|---|---|---|
| Type 3 | 35.0 $\mu$m | 1.3780 mils |
| Type 4 | 29.0 $\mu$m | 1.1417 mils |
| Type 5 | 20.0 $\mu$m | 0.7874 mils |
| Type 6 | 10.0 $\mu$m | 0.3937 mils |

In general, different types of solder paste often vary in grain size. Table 4 lists the nominal grain sizes associated with the various types of solder paste. In one embodiment of the invention, the variation in grain size results in a minimum magnification with which the solder paste deposit 102a may be sampled effectively by a CCD camera 104.

If a set of system magnifications (measured in microns or mils per pixel) is selected so that each of the solder paste types shown in Table 4 is sampled at the Nyquist limit, then a table of compatible magnifications can be created as shown below in Table 5.

TABLE 5

Compatible system magnifications for various types of solder paste where X indicates compatible magnification and the system magnification is shown in microns ($\mu$m) and mils per pixel (mpp).

| | 5.0 $\mu$m 0.1969 mpp | 10.0 $\mu$m 0.3937 mpp | 14.5 $\mu$m 0.5709 mpp | 17.5 $\mu$m 0.6890 mpp |
|---|---|---|---|---|
| Type 3 | X | X | X | X |
| Type 4 | X | X | X | — |
| Type 5 | X | X | — | — |
| Type 6 | X | — | — | — |

In theory, the Nyquist limit is the highest frequency, or in this case the smallest grain size, that may be accurately sampled at a given system magnification. The Nyquist limit may be defined as half of the sampling rate.

As discussed, the method of solder paste texture recognition relies on the unique neighborhood features and statistics of solder paste that are pronounced when the image is in sharp focus. In one embodiment of the invention, optical and imaging hardware is utilized to accurately sample the paste texture. In that embodiment, the sampling frequency of the paste particles is below the Nyquist limit of the system to avoid aliasing. Alternatively, magnification is generally limited so that the unique frequency characteristic of the solder paste is not lost, and where limited aliasing is acceptable, since the resultant characteristics of the image data, specifically in paste regions, may still be used to detect evidence of the paste.

In one embodiment of the invention, the performance of the processor 116 is optimized within an appropriate range of magnification by applying a frequency dependent kernel size and shape. Neighborhood pixels that lie an appropriate distance from the primary pixel (usually the central pixel) can manually, or automatically be selected based upon spatial frequency of the paste particles. By adjusting the geometry of the processing kernels in this manner, the effective sampling rate can be adjusted to accommodate various paste types. In one embodiment of the invention, the sensor sampling frequency is proportional to the reciprocal pixel center to center spacing measured in cycles per millimeter, and the highest frequency that may be accurately sampled is one-half the sensor sampling frequency. The magnification may also be described as a function of the pixel distribution patterns used to capture or process the image of the solder paste regions.

FIGS. 8A–8H show various pixel distribution patterns used to recognize the solder paste deposits over a region. The pixel distribution patterns represent sample kernel configurations for paste texture spacing configurations. The pixel distribution pattern used for magnification depends upon the grain size of the solder paste. In FIGS. 8A–8B and 8E–8F, the pixel distribution pattern shows the central pixels and neighboring pixels touching. In FIGS. 8C–8D and 8G–8H, the central pixels and neighboring pixels are shown separated by various distances. The distances are represented by diameters (measured in microns and mils) of a circle centered on the central pixel. The radius corresponds to the effective pixel spacing, or the sampling rate. Therefore, the diameter represents the Nyquist limit, or the minimum theoretical paste grain size that can be sampled effectively using the indicated kernel geometry. In one embodiment of the invention shown in FIGS. 8A–8D, each pixel represents 0.6621 mils, and the circled regions of interest vary in diameter from 1.3242 mils to 3.7454 mils. In FIGS. 8E–8H, each pixel represents 0.4797 mils, and the circled regions of interest vary in diameter from 0.9594 mils to 2.7136 mils.

Kernel configurations are not limited to those shown in FIGS. 8A–8H and, in general, no connectivity between the pixels is required.

Experimental Results

As discussed above, one embodiment of the invention uses a combination of statistical and morphological operations on a digitized image to separate areas of solder paste texture areas from other feature-rich non-paste areas on a printed circuit board, stencil, wafer, or any substrate. FIGS. 9A–9D show the results of a system that utilizes an embodiment of the invention.

Figure 9A:
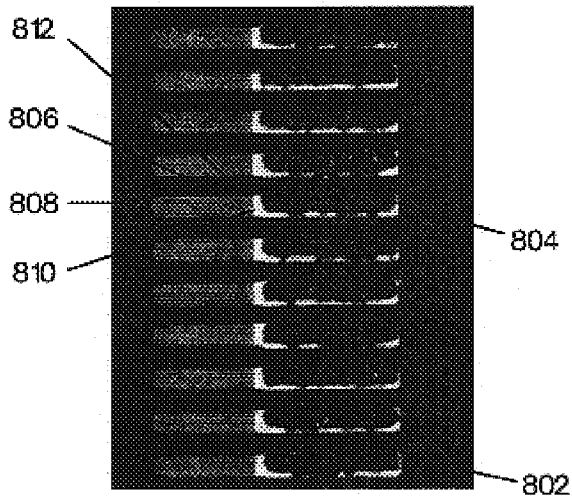
FIGS. 9A–9D is a representation of experimental results from a system that utilizes an embodiment of the invention.

Shown in FIG. 9A is raw image data, with no saturation, of a printed circuit board 802 having solder paste areas 804 and non-paste features distributed thereon. The raw image shows a well defined edge 806 that outlines a circuit trace 808 leading to a contact region 810, and a well defined separation line 812 that begins the contact region.

Figure 9B:
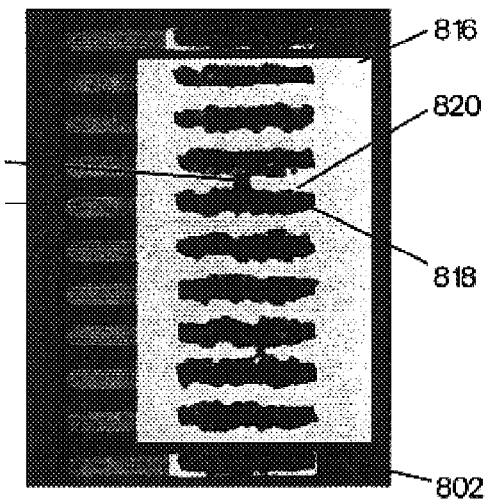

In FIG. 9B, the results of a processed image using the method of the invention is shown. The processed image reveals a solder bridge 814 not seen in FIG. 9A. Note that the non-paste features including edge 806, trace 808, contact region 810, and separation line 812 shown in FIG. 9A are shown as white areas in the region of interest 816, while the solder paste regions 818 are shown as black. Since in the output image the presence of solder paste is represented by a black region, any region that is not totally black or white indicates a scalable transitional region at paste edges or some other area of uncertainty at that location. Accordingly, the gray scalable regions 820 improve the ability to accurately report the location and area of small paste deposits where edges constitute a large percent of the total area and, under certain conditions, is more tolerant of variations in image quality, brightness, and contrast.

Figure 9C:
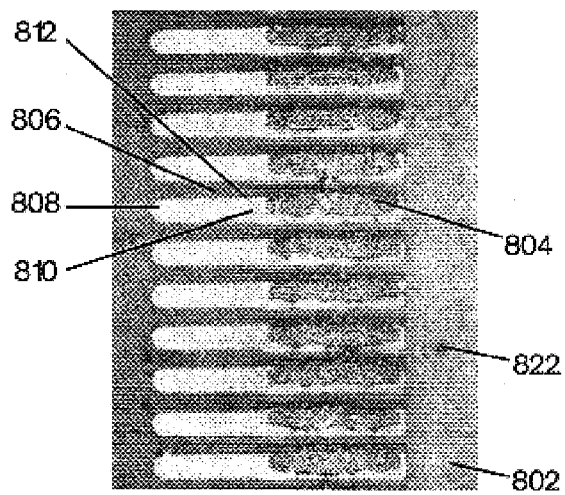

Shown in FIG. 9C is the raw image, with saturation, of the same printed circuit board 802 having solder paste areas 804 and non-paste features distributed thereon. The raw image shows the same well defined edge 806 that outlines a circuit trace 808 leading to a contact region 810. However, the well defined separation line 812 shown in FIG. 9A, and the gray level representation of trace 808 and the contact pads 810, are indistinguishable in FIG. 9C. FIG. 9C also shows a blemish 822 on the printed circuit board not observed in any of the previous images.

Figure 9D:
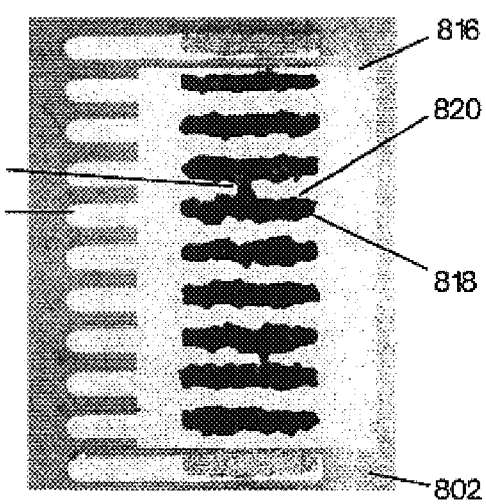

FIG. 9D is the raw image, with saturation, processed utilizing the method of the invention. The processed image shown in FIG. 9D reveals a solder bridge 814. The non paste features 816 are shown in FIG. 9D as white, paste edges 820 and areas of uncertainty in gray, and the solder paste regions 818 are shown as black and represent areas in which 100 percent solder paste is detected. Note that non solder paste regions, including the blemish 822 shown in FIG. 9C, on the substrate are ignored when the method of the invention is applied. The gray levels are scalable areas that represent regions that lie between the non-essential features on a printed circuit board and the solder paste deposits. The gray scale information allows proportional accounting of edge pixels and any areas of uncertainty. Accordingly, the scalable gray areas convey more information to an observer regarding the quality of the solder paste contact region than a binary image that is either black or white.

Figure 10A:
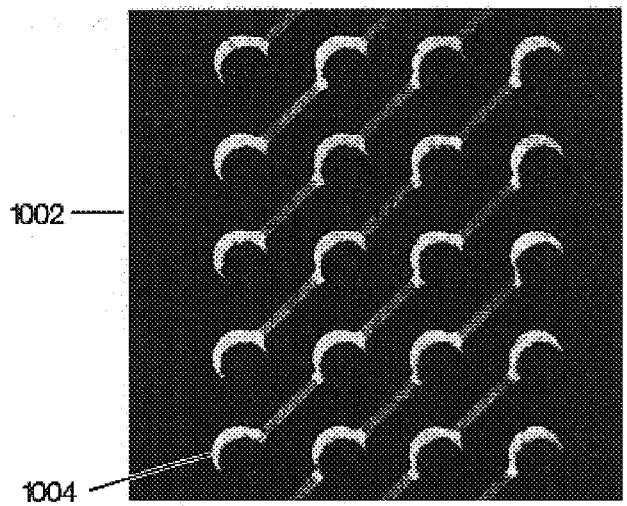
FIGS. 10A–10C is a comparison of raw images from a system that utilizes an embodiment of the invention without saturation.
Figure 10B:
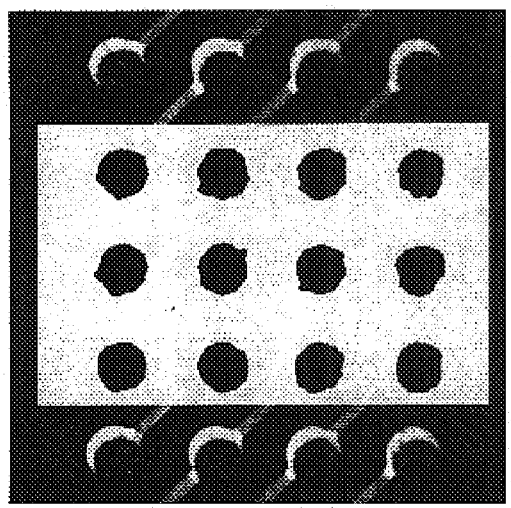
Figure 10C:
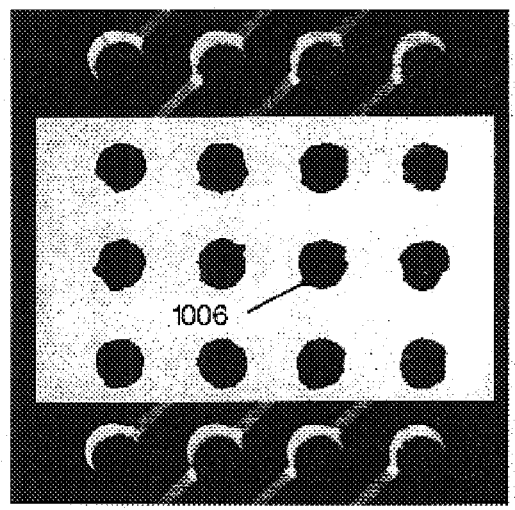
Figure 11A:
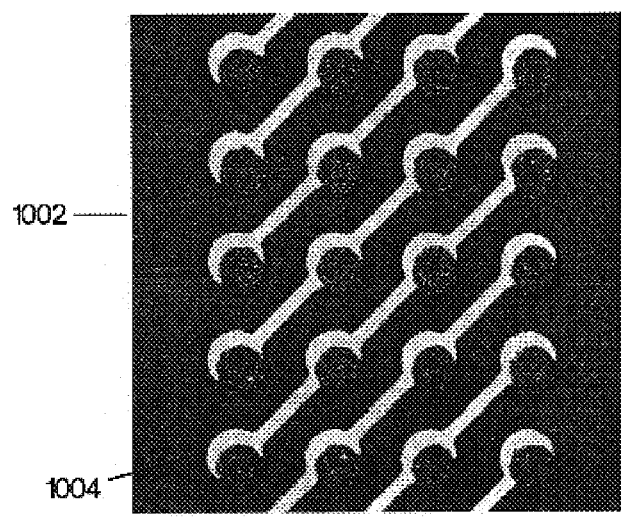
FIGS. 11A–11C is a comparison of raw images from a system that utilizes an embodiment of the invention with saturation.

FIGS. 10A–10C and FIGS. 11A–11C provide a comparison of images from a system that utilizes an embodiment of the invention. FIG. 11A shows the same raw image of FIG. 10A except with saturation. The raw images are processed utilizing the method of the invention. The processed images may be made binary, i.e., black or white, by application of a single thresholding technique, or the processed images may have a scalable gray range by application of a dual thresholding technique. As previously described, dual thresholds make it possible to appropriately account for transitional regions at paste edges and other areas of uncertainty. Accordingly, the method of the invention improves the ability of quality control software programs to accurately report the area of small paste deposits where edges constitute a large percent of the total area, and the method of the invention is more tolerant of variations in image quality, brightness, and contrast.

FIGS. 10A–10C show a series of ball grid array (BGA) images for comparison between a raw image without saturation when single and dual threshold processes are performed on the image. FIG. 10A shows an unprocessed raw BGA image 1002 without saturation, and an array of predetermined contact pads 1004. FIG. 10B shows the results of a single threshold process performed on the raw BGA image shown in FIG. 10A. FIG. 10C shows the results of a dual threshold process utilizing scalable gray levels performed on the raw BGA image shown in FIG. 10A. Edges and regions of uncertainty are in shades of gray. One region of uncertainty appears at 1006.

Figure 11B:
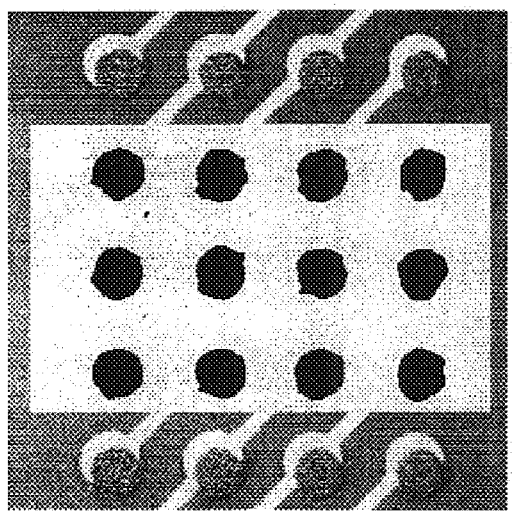
Figure 11C:
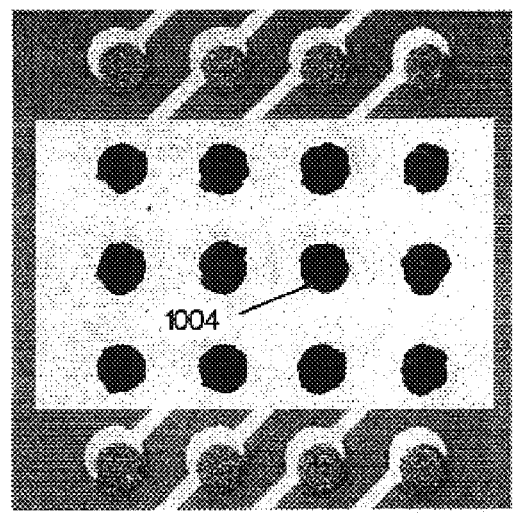

FIGS. 11A–11C show a series of BGA images for comparison with the raw BGA image 1002 with saturation when a single threshold process and a dual threshold process are performed on the image. FIGS. 11A–11C also serves as a comparison of images from a ball grid array (BGA) from a system that utilizes an embodiment of the invention with saturation. FIG. 11A shows an array of predetermined contact pads 1004, and an unprocessed raw BGA image 1002 with saturation. FIG. 11B shows the results of a single threshold process performed on the raw BGA image 1002 of FIG. 11A. FIG. 11C shows the results of a dual threshold process utilizing scalable gray levels performed on the raw BGA image of FIG. 11A. Edges and regions of uncertainty are in shades of gray. The same region of uncertainty 1006 appears in both FIG. 10C and FIG. 11C.

FIGS. 10B–C and FIGS. 11B–C show that the method of the invention is tolerant of significant image brightness and contrast variations in non-paste features, including non-linear brightness changes, and data loss due to saturation or drop-out of non-paste features.

Figure 12:
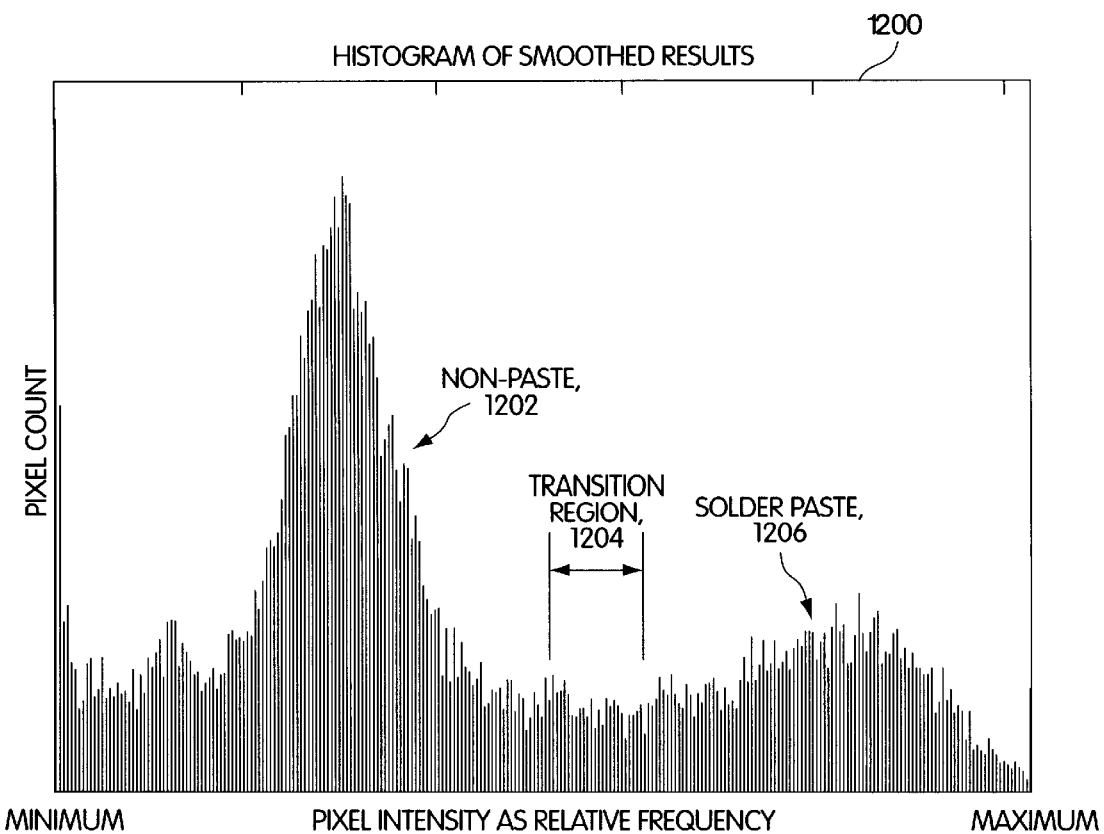
FIG. 12 is a histogram of experimental results from a system that utilizes an embodiment of the invention.

FIG. 12 shows a histogram 1200 of the smoothed results of a system that utilizes an embodiment of the invention. The histogram is divided into three regions: a non-paste region 1202, a transition region 1204, and a solder paste region 1206. The histogram 1200 shows a distribution of pixel brightness which corresponds to the texture in the smoothed image. In one embodiment, the smoothed image depicts paste as white and non-paste as black. Accordingly, paste pixels 1206 favor the right end of the histogram and non-paste pixels 1202 favor the left end. Transitional pixels 1204 corresponding to an edge in the image is shown in the area between the paste and non-paste regions. In another embodiment of the invention, the smoothed image is inverted to depict paste as black and non-paste as white.

Embodiments of the present invention overcome problems associated with prior solder paste inspection systems associated with stencil printers by utilizing a method that effectively removes non essential background features and highlights the solder paste regions on a printed circuit board. However, a person skilled in the art understands that the method and apparatus described herein may be associated with inspecting materials other than solder paste, and that the method may be utilized in apparatuses other than stencil printers.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A screen printer for dispensing a viscous material at a predetermined location on a substrate comprising:
    a frame;
    a material dispenser, coupled to the frame, the material dispenser containing a viscous material to be printed on a substrate;
    a support apparatus, coupled to the frame, that supports the substrate in a printing position located beneath the material dispenser;
    a camera having a field of view that includes an image of the substrate; and
    a processor in electrical communication with the camera, the processor being programmed to perform texture recognition on the viscous material printed on the substrate the processor comprising:
        a locator that performs location analysis on various pixels in the image;
        a tuner that varies brightness and contrast levels in the image and includes an automatic gain, offset, and exposure management system wherein the tuner provides aliasing control based on an effective sampling rate; and
        a texture segmentation filter, in electrical communication with the locator, that includes at least one of a sharpening operator, a Laplace operator, and a smoothing operator.

2. The screen printer of claim 1 wherein the viscous material includes solder paste.

3. The screen printer of claim 2 wherein the texture segmentation filter divides the image into texture regions.

4. The screen printer of claim 2 wherein the smoothing operator includes a mechanism for boosting said texture segmentation filter.

5. The screen printer of claim 2 wherein the processor is part of a control loop that comprises a controller in electrical communication with the material dispenser.

6. The screen printer of claim 1 wherein the texture segmentation filter includes a sharpening operator, a Laplace operator, and a smoothing operator.

7. A screen printer that dispenses a viscous material at a predetermined location on a substrate comprising:
    a frame;
    a dispenser, coupled to the frame, the material dispenser containing a viscous material to be printed on a substrate;
    a support, coupled to the frame, that supports the substrate in a printing position located beneath the material dispenser;
    a camera positioned to view the substrate; and
    a processor means in electrical communication with the camera, the processor for performing texture recognition on the viscous material printed on the substrate, the processor comprising:
        a locator that performs location analysis on various pixels in the image;
        a tuner that varies brightness and contrast levels in the image and includes an automatic gain, offset, and exposure management system wherein the tuner provides aliasing control based on an effective sampling rate; and
        a texture segmentation filter, in electrical communication with the locator, that includes at least one of a sharpening operator, a Laplace operator, and a smoothing operator.

8. The screen printer of claim 7 wherein the viscous material includes solder paste.

9. The screen printer of claim 7 wherein the camera includes a charge coupled device.

10. The screen printer of claim 7 wherein the texture segmentation filter divides the image into texture regions.

11. The screen printer of claim 7 wherein the smoothing operator includes a mechanism for boosting said texture segmentation filter.

12. The screen printer of claim 7 wherein the texture segmentation filter includes a sharpening operator, a Laplace operator, and a smoothing operator.

13. The screen printer of claim 7 wherein the processor is part of a control loop that comprises a controller in electrical communication with the material dispenser.

14. A system for dispensing solder paste at a predetermined location on a substrate comprising:
    a dispenser that dispenses material on the substrate;
    a controller for maintaining the operations of the dispenser; and
    a processor in electrical communication with the controller the processor being programmed to perform texture based recognition of a solder paste deposit located on the substrate and to determine the quality of the solder paste deposit and the contours of the solder paste deposit relative to predetermined locations on the substrate, the processor comprising:
        a locator that performs location analysis on various pixels in the image;
        a tuner that varies brightness and contrast levels in the image and includes an automatic gain, offset, and exposure management system wherein the tuner provides aliasing control based on an effective sampling rate; and
        a texture segmentation filter, in electrical communication with the locator, that includes at least one of a sharpening operator, a Laplace operator, and a smoothing operator.

15. The system of claim 14 wherein the texture segmentation filter divides the image into texture regions.

16. The system of claim 14 wherein the smoothing operator includes a mechanism for boosting said texture segmentation filter.

17. The system of claim 14 wherein the processor is part of a control loop that comprises the controller in electrical communication with the dispenser.

18. The system of claim 17 wherein the controller adjusts alignment of the stencil printer and the stencil.

19. The screen printer of claim 14 wherein the texture segmentation filter includes a sharpening operator, a Laplace operator, and a smoothing operator.

20. An inspection system for detecting the presence and location of a substance on a substrate comprising:

a locator that performs location analysis on various pixels in an image of the substance on the substrate; and a processor in electrical communication with the locator, said processor being programmed to perform texture based recognition of the substance located on the substrate, and to determine the quality of the solder paste deposit and the contours of the solder paste deposit relative to predetermined locations on the substrate, the processor including a tuner that varies brightness and contrast levels in the image and includes an automatic gain, offset, and exposure management system wherein the tuner provides aliasing control based on an effective sampling rate.

21. The inspection system of claim 20 wherein the processor is part of a control loop that comprises a controller in electrical communication with a material dispenser that dispenses the substance onto the substrate.

22. The system of claim 21 wherein the controller adjusts alignment of the stencil printer and the stencil.

23. The inspection system of claim 20 wherein the substance includes solder paste.

24. The inspection system of claim 20 further comprising a texture segmentation filter that includes at least one of a sharpening operator, a Laplace operator, and a smoothing operator.

25. The inspection system of claim 24 wherein said smoothing operator includes a mechanism for boosting said texture segmentation filter.

26. The inspection system of claim 20 wherein a fill-factor option is provided to increase the speed of detecting the presence and location of a substance on a substrate.

27. The inspection system of claim 20 further comprising a texture segmentation filter that includes a sharpening operator, a Laplace operator, and a smoothing operator.

* * * * *